United States Patent
Silvestrini

(10) Patent No.: US 10,973,850 B2
(45) Date of Patent: Apr. 13, 2021

(54) COMPOSITION COMPRISING TRICALCIUM PHOSPHATE AND GELATIN FOR USE IN A METHOD FOR THE TREATMENT OF DYSPEPSIA AND RELATED DISORDERS

(71) Applicant: S.B.M. S.R.L., Rome (IT)

(72) Inventor: Bruno Silvestrini, Rome (IT)

(73) Assignee: Health Pharma S.p.A., Bolzano (IT)

( * ) Notice: Subject to any disclaimer, the term of this patent is extended or adjusted under 35 U.S.C. 154(b) by 0 days.

(21) Appl. No.: 15/542,336

(22) PCT Filed: Jan. 8, 2016

(86) PCT No.: PCT/EP2016/050275
§ 371 (c)(1),
(2) Date: Jul. 7, 2017

(87) PCT Pub. No.: WO2016/110567
PCT Pub. Date: Jul. 14, 2016

(65) Prior Publication Data
US 2018/0271905 A1 Sep. 27, 2018

(30) Foreign Application Priority Data
Jan. 9, 2015 (EP) .................................... 15425001

(51) Int. Cl.
| | | |
|---|---|---|
| A61K 33/42 | (2006.01) | |
| A61K 38/39 | (2006.01) | |
| A61K 47/42 | (2017.01) | |
| A61K 9/00 | (2006.01) | |
| A61K 9/20 | (2006.01) | |
| A61P 1/14 | (2006.01) | |
| A61K 45/06 | (2006.01) | |

(52) U.S. Cl.
CPC ............ *A61K 33/42* (2013.01); *A61K 9/0056* (2013.01); *A61K 9/0095* (2013.01); *A61K 9/20* (2013.01); *A61K 9/2063* (2013.01); *A61K 38/39* (2013.01); *A61K 45/06* (2013.01); *A61K 47/42* (2013.01); *A61P 1/14* (2018.01)

(58) Field of Classification Search
CPC ...... A61K 33/42; A61K 47/42; A61K 9/0095; A61K 9/2063; A61K 9/0056; A61K 9/20; A61K 45/06; A61K 38/39; A61P 1/14
See application file for complete search history.

(56) References Cited

U.S. PATENT DOCUMENTS

| | | | | |
|---|---|---|---|---|
| 3,564,097 | A * | 2/1971 | Magid .................... | A61K 9/2009 424/602 |
| 6,645,535 | B2 * | 11/2003 | Zyck ....................... | A23G 4/00 424/440 |
| 2007/0219128 | A1 | 9/2007 | Chen et al. | |
| 2007/0292517 | A1 * | 12/2007 | Farber .................... | A61K 9/0056 424/488 |
| 2014/0154388 | A1 * | 6/2014 | Atapattu ................ | A23C 20/00 426/582 |

FOREIGN PATENT DOCUMENTS

| | | | | |
|---|---|---|---|---|
| WO | 2010092468 A1 | 8/2010 | | |
| WO | WO-2010092468 A1 * | 8/2010 | ............. | A61K 9/107 |
| WO | WO-2012160575 A2 * | 11/2012 | ................ | A23J 1/10 |

OTHER PUBLICATIONS

Dale, Jack K., and Roger E. Booth. "A study of antacids." Journal of the American Pharmaceutical Association (Scientific ed.) 44.3 (1955): 170-177.*
Fujishiro, M., et al. "Endoscopic spraying of sucralfate using the outer sheath of a clipping device." Endoscopy 34.11 (2002): 935-935.*
European Office Action issued in European Patent Application No. 16700191.6 dated Aug. 3, 2018.
Chinese Office Action issued in Chinese Patent Application No. 201680005358 dated Jan. 2, 2020.
"Patient endorses remedy for mouth lesions", Dr. Gott, http://askdrgottmd.com/patient-endorses-remedy-for-mouth-lesions/,1-2.
Arents NLA et al.,"A rational approach to uninvestigated dyspepsia in primary care: review of the literature" Postgrad Med J 2002, 78, p. 707-716.
R.J. Saad et al., "Review article: current and emerging therapies for functional dyspepsia" Alimentary Pharmacology & Therapeutics, 24, pp. 475-492.
H.B. El-Serag et al., "Systematic review: the prevalence and clinical course of functional dyspepsia" Aliment Pharmacol Ther, 2004, 19, pp. 643-654.
Sanjiv Mahadeva et al., "Epidemiology of functional dyspepsia: A global perspective" World Journal of Gastroenterology, May 7, 2006, vol. 12, No. 17, pp. 2661-2666.
Salvatella M. et al., "Inhibition of acid secretion by the nonsteriodal anti-inflammatory drugs diclofenac and piroxicam in isolated gastric glands: analysis of a multifocal mechanism" Am J Physiol Gastrointest Liver Physiol, vol. 286, May 2004, pp. G711-G721.
Hernandez-Diaz S. et al., "Association Between Nonsteriodal Anti-inflammatory Drugs and Upper Gastrointestinal Tract Bleeding/Perforation." Arch Intern Med, vol. 160, Jul. 24, 2000, pp. 2093-2099.
Higuchi K. et al., "Present status and strategy of NSAIDs-induced small bowel injury", J Gastroenterol, 2009, vol. 44, pp. 879-888.
Monkemuller K. et al., "Drug treatment of functional dyspepsia", World Journal of Gastroenterology, vol. 12, No. 17, May 7, 2006, pp. 2694-2700.
Johnson D. et al., "Perspectives in Clinical Gastroenterology and Heptatology", Clinical Gastroenterology and Heptatology, May 2013, vol. 11, No. 5, pp. 458-464.
Pali-Scholl I. et al., "Anti-acid medication as a risk factor for food allergy" Allergy 2011, 66, pp. 469-477.

(Continued)

*Primary Examiner* — John Pak
*Assistant Examiner* — Daniel L Branson
(74) *Attorney, Agent, or Firm* — Arent Fox LLP

(57) ABSTRACT

A pharmaceutical composition comprising tricalcium phosphate and gelatin for use in a method for the treatment of dyspepsia, acidic mouth and and/or canker sores is disclosed.

9 Claims, No Drawings

(56) References Cited

OTHER PUBLICATIONS

Diesner S.C. et al., "Dose-dependent food allergy induction against ovalbumin under acid-supression: A murine food allergy model" Immunol Lee., Nov. 16, 2008, 121(1), 45-51.
Untersmayr E. et al., "Anti-ulcer drugs promote IgE formation toward dietary antigens in adult patients", The FASEB Journal, Jan. 25, 2005.
Untersmayr E. et al., "Antacid medication inhibits digestion of dietary proteins and causes food allergy: A fish allergy model in Balb/c mice" J Allergy Clin Immunol, vol. 112, No. 3, Sep. 2003, pp. 616-623.
Wilson D. et al., "Effects of Misoprostol on Gastric Acid and Mucus Secretion in Man", Digestive Diseases and Sciences, vol. 31, No. 2, Feb. 1986, pp. 126S-129S.
O.S. Tang et al., "Misoprostol: Pharmacokinetic profiles, effects on the uterus and side effects" Internation Journal of Gynecology and Obstetrics, 2007, 99, pp. S160-S167.
Lemann J. et al., "The Effects of Chronic Acid Loads in Normal Man: Further Evidence for the Participation of Bone Mineral in the Defense against Chronic Metabolic Acidosis", Journal of Clinical Investigation, vol. 45, No. 10, 1966, pp. 1608-1614.
Green et al., "Role of bone in regulation of systemic acid-bade balance" Kidney International, vol. 39, 1991, pp. 9-26.

\* cited by examiner

COMPOSITION COMPRISING TRICALCIUM PHOSPHATE AND GELATIN FOR USE IN A METHOD FOR THE TREATMENT OF DYSPEPSIA AND RELATED DISORDERS

CROSS-REFERENCE TO RELATED APPLICATION

This application is a 35 U.S.C. 371 National Phase of PCT Application No. PCT/EP2016/050275 filed Jan. 8, 2016 which claims priority to EP Application No. EP 15425001.3 filed Jan. 9, 2015. The disclosure of these prior applications are hereby incorporated by reference herein.

FIELD OF THE INVENTION

The present invention relates to the pharmaceutical field and more in particular to a pharmaceutical composition comprising tricalcium phosphate and gelatin for use in a method for the treatment of dyspepsia and related disorders.

STATE OF THE ART

Dyspepsia—literally, "indigestion" from the ancient Greek δυσπέψις—is a medical condition characterized by chronic or recurrent pain in the upper abdomen, associated with bloating, belching, nausea, heartburn, gastro esophageal reflux, vomiting (Arents N, Thijs J and Kleibeuke J. A rational approach to uninvestigated dyspepsia in primary care: review of the literature. Postgrad Med J. 2002; 78(926): 707-716; Dorland's Illustrated Medical Dictionary, 32nd Edition, 2011; Heading RC. Definitions of dyspepsia. Scand J Gastroenterol 1991; 26(182):1-6; Yamada T, Alpers D H, et al. Textbook of gastroenterology (5th ed.). Chichester, West Sussex: Blackwell Pub. 2009; pp. 2774-2784; Saad R J and Chey W D. "Review article: current and emerging therapies for functional dyspepsia". Aliment. Pharmacol. Ther. 2006; 24(3):475-492; Talley N J and Vakil N. Guidelines for the management of dyspepsia. Am. J. Gastroenterol. 2005; 100(10):2324-2337; Zajac, P; Holbrook, A; Super, M E; Vogt, M. An overview: Current clinical guidelines for the evaluation, diagnosis, treatment, and management of dyspepsia. Osteopathic Family Physician 2013; 5(2):79-85). It affects about 15 percent of the general population in western countries, probably more in China, India and Japan (Shaib Y and El-Serag H B. The prevalence and risk factors of functional dyspepsia in a multiethnic population in the United States. Am J Gastroenterol 2004; 99:2210-2216; El-Serag H and Band Talley N J. Systemic review: The prevalence and clinical course of functional dyspepsia. Aliment Pharmacol Ther 2004; 19:643-654). In a percentage of cases varying between 11 to 29 percent, there is no evidence of a precise organic or otherwise detectable cause that is likely to explain its symptoms (Mahadeva S and Goh K L. Epidemiology of functional dyspepsia: A global perspective. World J Gastroenterol. 2006; 12(17): 2661-2666). The remaining cases are attributable to various causes, including *Helicobacter pylori* infection, medical treatments, peptic ulcer, cancer, and other diseases (Yamada T, Alpers D H, et al. Textbook of gastroenterology (5th ed.). Chichester, West Sussex: Blackwell Pub. 2009; pp. 2774-2784).

All forms of dyspepsia, including those with no detectable cause, have in common two interconnected pathogenetic factors: an excessive secretion of hydrochloric acid (HCl) and a failure of the mucus secretion that covers and protects the internal surface of the stomach. Non-steroidal antiinflammatory drugs (NSAIDs) provide a typical example of the second factor. Rather than increasing the acid secretion (Salvatella M, Rossi I, Del Valle J C, Gutierrez Y, Pereda C, Samper B, Feliu J E. Inhibition of acid secretion by the nonsteroidal anti-inflammatory drugs diclofenac and piroxicam in isolated gastric glands: analysis of a multifocal mechanism. Am J Physiol Gastrointest Liver Physiol. 2004; 286(5):711-721), they depress the prostaglandin-related mucus secretion in the stomach (Vane J R. Inhibition of prostaglandin synthesis as a mechanism of action for aspirin-like drugs. Nature New Biol. 1971; 231:232-235). Hence, a risk of low acidity dyspepsia eventually associated with ulcers, gastrointestinal bleeding and perforations (Hernandez-Diaz S. and Rodriguez L A. Association between nonsteroidal anti-inflammatory drugs and upper gastrointestinal tract bleeding/perforation: An overview of epidemiologic studies published in the 1990s. Arch Intern Med. 2000; 160: 2093-2099; Higuchi K, Umegaki E, Watanabe T, Yoda Y, Morita E, Murano M, Tokioka S, Arakawa T Present status and strategy of NSAIDs-induced small bowel injury. Journal of Gastroenterology. 2009; 44(9):879-888; Hirofumi Matsui, Osamu Shimokawa, Tsuyoshi Kaneko, Yumiko Nagano, Kanho Rai and Ichinosuke Hyodo. The pathophysiology of non-steroidal anti-inflammatory drug (NSAID)-induced mucosal injuries in stomach and small intestine. J Clin Biochem Nutr. 2011; 48(2):107-111; Ivet K J, Poane D B, Krause W K. Acute effects of systemic aspirin on gastric mucosa in man. Dig Dis Sci 1980: 25:97-99 Schoen R T and Vender R J. Mechanisms of nonsteroidal anti-inflammatory drug-induced gastric damage. The American Journal of Medicine. 1989; 86: 449-458; Wallace J L. Pathogenesis of NSAID-induced gastroduodenal mucosal injury. Best Pract Res Clin Gastroenterol. 2001; 15(5):691-703). The combination of the above pathogenetic factors exposes the gastric mucosa to erosion, resulting in activation of painful nervous terminals and upper abdomen pain.

Current medical treatments of dyspepsia focus on the excess of acidity. Antacids consist of a salt of an alkaline ion with a counter ion, such as calcium carbonate or magnesium and aluminium salts in various combinations (Maton P N and Burton M E. Antacids revisited a review of their clinical pharmacology and recommended therapeutic use. Drugs 1999; 57(6):855-870). They neutralize acidity by increasing the pH. Antacids in current use are associated with various side effects (Maton P N and Burton M E. Antacids revisited a review of their clinical pharmacology and recommended therapeutic use. Drugs 1999; 57(6):855-870; Talley N J and Vakil N. Guidelines for the management of dyspepsia. Am. J. Gastroenterol. 2005; 100(10):2324-2337). Magnesium hydroxide may cause diarrhea, calcium and aluminum constipation. High doses of carbonate and bicarbonate may cause alkalosis, which results in altered excretion of drugs, and possibly kidney stones. A chemical reaction between carbonate and HCl produces carbon dioxide gas, causing gastric distension. Aluminum hydroxide leads to insoluble aluminium-phosphate-complexes, with a risk of hypophosphatemia and osteomalacia. Although aluminium has a low gastrointestinal absorption, accumulation may occur in the presence of renal insufficiency.

Alternatively to antacids, the $H_2$ receptor antagonists were the first class of inhibitors of HCl secretion by gastric cells. The more effective proton pump inhibitors (Zajac, P; Holbrook, A; Super, M E; Vogt, M. An overview: Current clinical guidelines for the evaluation, diagnosis, treatment, and management of dyspepsia. Osteopathic Family Physician 2013; 5(2):79-85) followed them. Erosive esophagitis and peptic ulcers are their preferential indications, but several evidence-based guidelines and literature prove an efficacy in dyspepsia as well (Mönkemüller K and Malfertheiner P. "Drug treatment of functional dyspepsia". World J. Gastroenterol. 2006; 12(17):2694-700). Commonly reported adverse effects include headache, nausea, diarrhea, abdominal pain, fatigue, and dizziness, but their relation to the medical treatment is debated (Johnson D A, Edward C and Oldfield E C IV. Reported Side Effects and Complications of Long-term Proton Pump Inhibitor Use. Dissecting the Evidence. Clin Gastroenterol Hepatol. 2013; 11(5):458-464).

Antacids and antisecretory agents have a common limit, which stems from their mode of action and the physiology of digestion (Pali-Schöll I and Jensen-Jarolim E. Anti-acid medication as a risk factor for food allergy. Allergy 2011; 66(4):469-477; Diesner S C, Knittelfelder R, Krishnamurthy D, Pali-Schöll I, Gajdzik L, Jensen-Jarolim E, and Untersmayr E. Dose-dependent food allergy induction against ovalbumin under acid-suppression: A murine food allergy model". Immunology Letters 2008; 121(1):45-51; Untersmayr E and Noémi B. "Anti-ulcer drugs promote IgE formation toward dietary antigens in adult patients". The FASEB Journal 2007; 19(6):656-658; Linsky A, Gupta K, Lawler E V, Fonda J R, Hermos J A. Antacids Increase Risk for Recurrent *Clostridium Difficile* Infection. Arch Intern Med. 2010; 170(9):772-778; Untersmayr E and Schöll I. "Antacid medication inhibits digestion of dietary proteins and causes food allergy: a fish allergy model in BALB/c mice". The Journal of allergy and clinical immunology 2003; 112(3):616-623). This limit is inherent in the reduction of gastric acidity, which involves a suppression of acid mediated break down of proteins, with the risk of developing food and drug allergies. This happens due to undigested proteins passing into the gastrointestinal tract. Reduced stomach acidity also impairs bioavailability of some drugs and absorption of essential elements, including iron and vitamins. Since the low pH of the stomach normally kills ingested bacteria, a reduction of acidity may increase the vulnerability to infection.

Medical treatments addressed to the failure of the gastric mucus secretion, are less numerous than antacids and antisecretory agents. Sucralfate is a complex of aluminum sulfate and sugar: besides displaying an antacid effect, it covers the internal surface of the stomach with a protective lining in substitution of mucus. Its most common side effect is constipation, followed by flatulence, headache, hypophosphatemia, dry mouth and bezoar formation. Another example is gelatin, the industrial derivative of collagen. It provides the stomach with a biological, rather than an artificial protective lining. In laboratory animals, fish and mammalian gelatin is active against gastric ulcers of different origin (Castro G A, Carvalho J E, Tinti S V, Possenti A, Sgarbieri V C. Anti-ulcerogenic effect of a whey protein isolate and collagen hydrolysates against ethanol ulcerative lesions on oral administration to rats. Journal of Medicinal Food. 2010; 13(1):83-90; Castro G A, Sgarbieri V C, Carvalho J E, Tinti S V, Possent, A. Protective effect of collagen derivatives on the ulcerative lesions caused by oral administration of ethanol. Journal of Medicinal Food 2007; 10(1): 154-158 Dingding Chen and Lizhong Gao. Medical and health-care uses of pufferfish Type I collagen extract and processes for producing said extract. 2007. US Patent No. 2007219128 A1; Guangli Mu and Xingfu Ma. Casing smooth muscle collagen preparation method and functional study. Intestine casing smooth muscle collagen, its preparation method and application. CN Patent No. 102020711 A; Zhou Xin, Han Yang, Xu Jianwen. Functional composition for improving gastrointestinal function, supplementing collagen as well as protecting skin, bones, joints and blood vessels. 2011, CN Patent No. 102132814 A). The main inconvenience of gelatin is swelling in water, which results in a stomach distension that jeopardizes its use in dyspeptic patients (Gareis H and Schrieber R. Gelatin Handbook: Theory and Industrial Practice. Weinheim: Wiley-VCH, 2007).

Misoprostol acts in a similar way as gelatin, although by a different mechanism of action. It consists of a synthetic prostaglandin E1 (PGE1). Instead of providing by itself a protective lining, it promotes the prostaglandin-related mucus secretion (Dajani E Z. Overview of the mucosal protective effects of misoprostol in man. Prostaglandins. 1987; 33(1):17-29; Wilson D E, Quadros E, Rajapaksa T, Adams A, Noar M. Effects of misoprostol on gastric acid and mucus secretion in man. Dig Dis Sci. 1986; 31(2):126-129). The most commonly reported adverse effect is diarrhea. Moreover, misoprostol is contra-indicated in pregnant women because it increases uterine tone and contractions in pregnancy, with a risk of abortions (Tang O S, Gemzell-Danielsson K, Ho P C. Misoprostol: Pharmacokinetic Profile, Effects on the Uterus and Side-effects. International Journal of Gynecology and Obstetrics 2007; 99:5160-5167).

International Patent Application N. PCT/IB2009/000254 discloses the combination of alginates with monoterpenes, such as limonene for the treatment of Gastro-Esophageal Reflux Disease.

International Patent Application with publication number WO 2010/092468 discloses the combination of alginates with natural non-pharmacological substances, eventually microencapsulated with gelatin, such as limonene and essential oils with anticholinesterase activity and optionally also comprising antacids including tricalcium phosphate for the treatment of Gastro-Esophageal Reflux Disease 0.

Canadian Patent N. CA2284184 discloses the combination of tricalcium phosphate with vitamin D3 for the treatment of osteoporosis, Vitamin D3 and calcium deficiencies and Paget's disease.

Acidic mouth is a medical condition characterized by a chronic excess of acidity in the oral cavity (Brad W, Neville DDS, Douglas D. Damm DDS, Carl M, Allen, Jerry E. (2002). Oral & maxillofacial pathology, Saunders Ed; Crossley H (2007). "Unraveling the mysteries of saliva: its importance in maintaining oral health. 2007 Gen Dent. 55(4): 288-296). It results from various concomitant factors, including acidic foods and drinks, xerostomia and dyspepsia with gastro-esophageal reflux. Acidity of bacterial origin is the main cause of dental cavities, minerals being pulled from the teeth when the oral pH is below 5.5. Acidic mouth occurs in about 14% of postmenopausal women, the female to male ration being as much as 33 to 1 (Brad W, Neville DDS, Douglas D. Damm DDS, Carl M, Allen, Jerry E. (2002). Oral & maxillofacial pathology, Saunders Ed; Mock D and Chugh D. Burning Mouth Syndrome. International Journal of Oral Science 2010; 2 (1):1-4). Canker sores, also called aphthous ulcers, are painful, small lesions that develop on the soft tissues in the mouth or at the base of gums (Scully C (2013). Oral and maxillofacial medicine: the basis of diagnosis and treatment (3rd ed.). Edinburgh: Churchill Livingstone). In most populations, about 20% of individuals are affected to some degree by canker sores (Cawson R A, Odell E W, Porter S (2008). Cawson's essentials of oral pathology and oral medicine (8th ed.). Churchill Livingstone Ed; Neville B W, Damm D D, Allen C M, Bouquot J E (2008). Oral & maxillofacial pathology (3rd ed.). Saunders Ed).

So far, no selective antacid medical treatment is available for acidic mouth and canker sores. The problem is the same as with dyspepsia. It stems from the difficulty so far encountered in reducing the excess of acidity, without disturbing the digestive processes and the somewhat related microbial flora in the mouth and stomach.

It is known the use of the so called "Vinci Solution®" (Monticello Drug Company, Jacksonville, Fla., USA) which comprises tricalcium phosphate together with other ingredients, such as sodium alum, calcium carbonate, sodium perborate monohydrate, sodium carbonate, magnesium trisilicate, sodium saccharin for the treatment of mouth sores (Dr. Gott: "Patient endorses remedy for mouth lesions", 10 Jan. 2014 (2014-01-10), pages 1-2, http://askdrgottmd.com/patient-endorses-remedy-for-mouth-lesions/).

It is known in the art the use of the so-called "Mi Paste®" (CG America Inc. Alsip, Ill., USA) based on the active ingredient RECALDENT®, made of milk-derived proteins, to treat acid mouth and avoid tooth decay (Y Gordon Rye: "Prevent the Causes of Tooth Decay With MI Paste: Guide to Dentistry", 13 Nov. 2009 (2009-11-13), pages 1-2, http://guidetodentistry.comjprevent-the-causes-of-tooth-decay-with-mi-paste/).

Technical Problem

The active ingredients or compositions known in the art for treating dyspepsia present several drawbacks.

Regarding commonly used antacids, magnesium hydroxide may cause diarrhea, calcium and aluminum constipation. High doses of carbonate and bicarbonate may cause alkalosis, which results in altered excretion of drugs, and possibly kidney stones. Carbonates may react with HCl thus producing carbon dioxide gas causing gastric distension. Aluminum hydroxide leads to insoluble aluminum-phosphate-complexes, with a risk of hypophosphatemia and osteomalacia. Although aluminum has a low gastrointestinal absorption, accumulation may occur in the presence of renal insufficiency.

The adverse effects of $H_2$ receptors antagonists are headache, nausea, diarrhea, abdominal pain, fatigue, and dizziness.

Both antacids and antisecretory agents, such as $H_2$ receptors antagonists, since reduce gastric acidity lead to the suppression of acid-mediated break down of proteins, which is related to the development of allergies against food and/or drugs.

Reduced stomach acidity also impairs drugs and essential elements gastrointestinal adsorption and reduce gut flora thus increasing the vulnerability to infections.

The drugs known in the art, which act on the gastric mucosa secretion, present also several side effects such as constipation, flatulence, headache, hypophosphatemia, dry mouth, benzoar formation and some of them are dangerous for pregnant woman.

There is a strong felt need in the field of pharmacology of alternative compositions for the treatment of dyspepsia and related medical conditions avoiding the drawbacks of the prior art and reducing the several side effects because being able to control the acidity peaks without disturbing the normal acidity involved in the physiology of digestion.

Selective Medical treatments based on the control of the acid condition of the mouth are not available for acidic mouth and canker sores.

The same inventor developed the present invention by applying the so-called "bone acidostat" belonging to the physiological system regulating the blood acid base balance (Green J and Kleeman C R. Role of bone in regulation of systemic acid-base balance. Kidney International 1991; 39:9-26; Lemann J, Litzow J R and Lennon E J. The effects of chronic acid loads in normal man: Further evidence for the participation of bone mineral in the defense against chronic metabolic acidosis. J Clin Invest 1996; 45:1608-1614) to the treatment of medical treatment of dyspepsia and related medical conditions, represented by acidic mouth and canker sore. The bone acidostat consists of the huge amounts of tricalcium phosphate (TCP) that are normally stored in the skeleton within a collagen embodiment. At normal pH values, TCP is an insoluble mineral, which supports and protects the soft parts of the body. TCP dissolves in conditions of metabolic acidity, when it enters the blood stream and neutralizes acidity by providing the exact quantity of calcium that is required to readjust the systemic acid base equilibrium. Unlike a manmade thermostat, consisting of a sensor that requires a separate cooling or freezing machine, the bone acidostat is a unique entity, where the two functions coincide. Collagen plays an ancillary role to TCP. It governs its deposition, while providing the mineral component of the skeleton with a certain degree of flexibility (Guyton, A C and Hall J E. Textbook of Medical Physiology (11 ed.). Philadelphia: Elsevier Saunders, 2006).

The elements of the bone acidostat belong to the functioning and composition of the body, are edible materials, are completely recyclable and, unlike the manmade antacids and antisecretory agents, do not leave potentially dangerous wastes.

The bone acidostat as known for the regulation of systemic acid-base balance is not applicable to the control of gastric acidity. Unlike the systemic acid-base balance, gastric acidity involves a wide range of pH values, each of them plays a specific role being dependent on the food composition and the stage of the digestion process, and being subject to different controls by the two branches of the autonomic nervous system, the proton pump $H^+/K^+$ ATPase, gastrin, histamine, vasoactive intestinal peptides, cholecystokinin, and secretin and so on.

According to the present invention, the bone acidostat has been changed to fit to the gastric environment, by providing a pharmaceutical composition comprising tricalcium phosphate and gelatin.

The acidostat was calibrated according to the physiology of digestion, wherein The gastric acidity activates the enzyme pepsinogen, which then becomes pepsin, at a pH ranging from 3.0 to 5.0.

Gelatin exerts the technical effect of creating a sheath around calcium minerals (Gareis H and Schrieber R. Gelatin Handbook: Theory and Industrial Practice. Weinheim: Wiley-VCH, 2007), therefore adjusting the TCP dissolution threshold and exerting a buffering effect to a pH of about 3;

Furthermore, to take full advantage of the sheath-like protective effect of gelatin on the gastric mucosa, its ratio to TCP was inverted, passing from about 1 to 9, as in the bone, to 6 to 1, as in the stomach.

The gelatin maybe a non-gelling gelatin having Bloom equal to zero, to avoid the gelling-related gastric distension, which in dyspeptic patients is disturbing, while maintaining the protective action against HCl. The Bloom value provides a practical index of the gelling power. It consists of measuring the weight required to depress the surface of a gelatin sample.

For the treatment of acidic mouth and canker sores, the acidostat is calibrated to a pH of 5.0-5.5, which corresponds to the level of acidity, which pulls minerals from the teeth. To this purpose, the order of the ratio of TCP to gelatin passed from 1 to 6 to 1 to 10. Moreover, a gelling gelatin appeared advantageous because muco-adhesive properties on the mucosa.

OBJECT OF THE INVENTION

Is therefore object of the present invention a pharmaceutical composition comprising tricalcium phosphate and gelatin for use in a method for the treatment of dyspepsia, acidic mouth and canker sores.

DETAILED DESCRIPTION OF THE INVENTION

The pharmaceutical composition of the present invention comprises tricalcium phosphate and gelatin.

Preferably gelatin has an index of the gelling power (Bloom) equal to zero.

Preferably, gelatin is of animal origin and more preferably is of fish origin.

Preferably the ratio of tricalcium phosphate to gelatin is 1 to 10, more preferably is 1 to 6.

Preferably the pharmaceutical composition of the present invention further comprises at least one pharmaceutically acceptable inert excipient. The person with ordinary skills in the field of pharmacology is able to choose any suitable inert excipient from those known in the art.

Optionally, the pharmaceutical composition of the present invention further comprises at least one antacid and/or antisecretory agent. The person with ordinary skills in the field of pharmacology is able to choose any suitable antacid and/or antisecretory agent from those known in the art.

The pharmaceutical composition may be under the form of oral dispersible tablet to swallow.

The pharmaceutical composition may be under the form of any liquid form to administer by oral route.

The pharmaceutical composition may be administered in a unitary dose wherein the amount of gelatin is 1.5 g and the amount of tricalcium phosphate is 0.25 g.

The pharmaceutical composition maybe administered in a unitary dose wherein the amount of gelatin is 1.5 g and the amount of tricalcium phosphate is 0.25 g for 3 or 4 times a day.

The pharmaceutical composition of the present invention is for use in the treatment of dyspepsia.

The pharmaceutical composition of the present invention is for use in the treatment of acidic mouth.

The pharmaceutical composition of the present invention is for use in the treatment of canker sores.

Preferably, in the pharmaceutical composition of the present invention for use treatment of acidic mouth and canker sores the ratio of tricalcium phosphate to gelatin is 1 to 10 and the gelatin is a gelling gelatin.

Preferably, in the pharmaceutical composition of the present invention for use treatment of dyspepsia the ratio of tricalcium phosphate to gelatin is 1 to 6 and the gelatin has an index of the gelling power (Bloom) equal to zero.

Preferably the pharmaceutical composition of the present invention is in the form of an oral dispersible tablet to swallow or in the form of a liquid for oral administration, when is for use in the treatment of dyspepsia.

Preferably the composition of the present invention is in the form of a tablet to swallow or in the form of a liquid, more preferably in a bottle with a spray dispenser, for oral administration when is for use in the treatment of acidic mouth or canker sores.

Preferably the pharmaceutical composition for use treatment of dyspepsia comprises tricalcium phosphate and gelatin, wherein gelatin is of animal origin and preferably of fish origin, which is under the form of an tablet or in a form of a liquid is administered orally in an unitary dose wherein the amount of gelatin is 1.5 g and the amount of tricalcium phosphate is 0.25 g for 3 or 4 time a day.

Preferably the pharmaceutical composition for use treatment of acidic mouth or canker sores comprises tricalcium phosphate and gelatin, wherein gelatin is of animal origin and preferably of fish origin, wherein the ratio of tricalcium phosphate to gelatin is 1 to 6, which is under the form of a tablet to swallow or in the form of a liquid, more preferably in a bottle with a spray dispenser, for oral administration.

In an embodiment of the present invention an oral dispersible tablet contains:

| | |
|---|---|
| 0 Bloom Gelatin | g 1.5000 |
| Tricalcium phosphate | g 0.2500 |
| Microcrystalline cellulose | g 0.1200 |
| Talc | g 0.0170 |
| Magnesium stearate | g 0.0170 |
| Licorice flavoring | g 0.0050 |
| Vanilla flavoring | g 0.0025 |
| Sucralose | g 0.0025 |

In an embodiment of the present invention a liquid formulation contains:

| | |
|---|---|
| Demineralized water | 91.19% |
| Hydroxyethycellulose | 1.00% |
| Gelatin | 1.00% |
| Tricalcium phosphate | 0.10% |
| Glycerol | 0.30% |
| Sorbitol | 0.20% |
| Potassium chloride | 0.12% |
| Monobasic potassium phosphate | 0.085% |
| Sodium chloride | 0.0843% |
| Calcium chloride | 0.01% |
| Magnesium chloride hexahydrate | 0.0024% |
| Sucralose | 0.01% |
| Sodium methylparaben | 0.15% |
| Potassium sorbate | 0.30% |
| Ethanol | 5.0% |
| Mint flavoring | 0.45% |

EXAMPLES

Example 1—Protective Effect

The barrier-like effect of gelatin was experimentally assessed. A Sheet of wheat starch was exposed to a concentrated solution of HCl. The protective action was measured as an extension of time to perforation in comparison to control. The end consisted of a clear-cut hole.

The experimental test showed that gelatin and TCP are almost equally effective, the first by its barrier-like action, the second as a buffer. When combined with gelatin, TCP displayed the dissolution-related buffering effect at higher HCl concentration than alone. The new threshold matched the potentially dangerous HCl concentration in the stomach at the above-mentioned ration, corresponding to about 6 parts of gelatin to 1 part of TCP.

Example 2—Preparation

Based on the above data and experimental results, TCP has been powdered and processed with a 0 Bloom gelatin as a solid powder or a liquid suspension, the ration of TCP to gelatin being of the order of 1 to 6. The unit dose, to repeat up to 3-4 times a day, is 0.25 g of TCP and 1.5 g of gelatin. The pharmaceutical form may consist of a tablet to desegregate in the mouth and swallow or of a liquid suspension.

The tablet contains:

| | |
|---|---|
| 0 Bloom Gelatin | g 1.5000 |
| Tricalcium phosphate | g 0.2500 |
| Microcrystalline cellulose | g 0.1200 |
| Talc | g 0.0170 |
| Magnesium stearate | g 0.0170 |
| Licorice flavoring | g 0.0050 |
| Vanilla flavoring | g 0.0025 |
| Sucralose | g 0.0025 |

TCP has been powdered and processed with gelatin as a liquid suspension, comprising a bottle with a spray dispenser containing:

| | |
|---|---|
| Demineralized water | 91.19% |
| Hydroxyethycellulose | 1.00% |
| Gelatin | 1.00% |
| Tricalcium phosphate | 0.10% |
| Glycerol | 0.30% |
| Sorbitol | 0.20% |
| Potassium chloride | 0.12% |
| Monobasic potassium phosphate | 0.085% |
| Sodium chloride | 0.0843% |
| Calcium chloride | 0.01% |
| Magnesium chloride hexahydrate | 0.0024% |
| Sucralose | 0.01% |
| Sodium methylparaben | 0.15% |
| Potassium sorbate | 0.30% |
| Ethanol | 5.0% |
| Mint flavoring | 0.45% |

Example 3—Effect on Dyspepsia

Preliminary data were collected by treating 35 patients, in about 2 years, with food supplement Bonartro® (S.B.M. Srl, Rome, Italy) containing collagen and TCP, a single daily dose of 7 g and 1 g respectively. Bonartro is currently prescribed in osteo-articular conditions (Adam M, Spacek P, Hulejova H, Galianova A and Blahos J. Postmenopausal osteoporosis. Treatment with calcitonin and a diet rich in cartilage proteins. Cas Lek Cesk, 1996; 135: 74-78; Beuker et al. Die Wirkung regelmäßiger Gelatinegaben auf chronisch-degenerative Schaden am Stutz-und Bewegungsapparat, Int. J. Sportsmed. 1996; 1:1-88; 3 Rippe J M et al. The effectiveness of collagen hydrolysate supplementation treatment in individuals with symptoms of mild osteoarthritis, EULAR-Kongress 2004). Unexpectedly pronounced relief of concomitant dyspepsia was observed, in about half of the cases was associated with the use of NSAIDs.

The tables as prepared in example 2 were administered to 85 patients suffering of dyspepsia. The improvement was assessed by a simplified score system, rating 0, +, ++, +++ according to the patient's personal judgment. Results were extremely positive, rating from ++ to +++ in the majority of patient (87%).

The above data and results indicated that a pharmaceutical composition comprising TCP and gelatin was also applicable, with obvious adjustments, to the medical treatment of acidic mouth and canker sores. The acidostat was calibrated to a pH of 5.0-5.5, which corresponds to the level of acidity, which pulls minerals from the teeth. To this purpose, the order of the ratio of TCP to gelatin passed from 1 to 6 to 1 to 10. Moreover, a gelling gelatin appeared advantageous because mucoadhesive properties on the mucosa. TCP has been powdered and processed with gelatin as a liquid suspension. A typical pharmaceutical composition, comprising a bottle with a spray dispenser, is given in the not limiting The liquid suspension of example 2 was tested on 10 persons having a saliva pH below 5.5. In all of them, acidy was neutralized following either a single or a double spraying, the effect lasting from 2 to four hours. Similar results are obtainable with oral solution to rinse or solid forms to dissolve in the mouth. The applications may be repeated initially up 3 times an hour, then once every 4-6 hours as a maintain treatment.

The invention claimed is:

1. A composition for the treatment of dyspepsia, acidic mouth and/or canker sores, the composition comprising tricalcium phosphate and gelatin, wherein the ratio of tricalcium phosphate to gelatin is about 1:6, and wherein the composition is in the form of an oral dispersible tablet to swallow or in the form of a liquid to be administered by oral route.

2. The composition according to claim 1, wherein the gelatin is of animal origin.

3. The composition according to claim 1, wherein the gelatin is of fish origin.

4. The composition according to claim 1, wherein the composition is in unit dose form comprising 1.5 g gelatin and 0.25 g tricalcium phosphate.

5. The composition according to claim 1, wherein the gelatin is of animal origin; and wherein the composition is in unit dose form comprising 1.5 g gelatin and 0.25 g tricalcium phosphate.

6. The composition according to claim 1 further comprising at least one antacid and/or antisecretory agent.

7. The composition according to claim 1, wherein the gelatin is of fish origin; and wherein the composition is in a unit dose form comprising 1.5 g gelatin and 0.25 g tricalcium phosphate.

8. A bottle with a spray dispenser for oral administration, comprising the composition according to claim 1, wherein the composition is in liquid form and wherein the gelatin is of animal origin.

9. A bottle with a spray dispenser for oral administration, comprising the composition according to claim 1, wherein the composition is in liquid form and wherein the gelatin is of fish origin.

\* \* \* \* \*